United States Patent [19]

Polaschegg

[11] Patent Number: 4,895,657
[45] Date of Patent: Jan. 23, 1990

[54] APPARATUS FOR HEMODIALYSIS

[75] Inventor: Hans-Dietrich Polaschegg, Oberursel, Fed. Rep. of Germany

[73] Assignee: Fresenius AG, Bad Homburg, Fed. Rep. of Germany

[21] Appl. No.: 253,814

[22] Filed: Oct. 5, 1988

[30] Foreign Application Priority Data

Oct. 15, 1987 [DE] Fed. Rep. of Germany ....... 3734880

[51] Int. Cl.$^4$ ........................................... B01D 13/00
[52] U.S. Cl. ..................................... 210/647; 210/85; 210/86; 210/96.2; 210/257.2; 210/321.71; 210/744; 210/746
[58] Field of Search ............... 210/85, 86, 96.2, 257.2, 210/321.71, 646, 647, 739, 744, 746

[56] References Cited

U.S. PATENT DOCUMENTS

| | | | |
|---|---|---|---|
| 4,150,673 | 4/1979 | Watt | 604/408 |
| 4,718,022 | 1/1988 | Cochran | 210/321.71 |
| 4,739,492 | 4/1988 | Cochran | 210/301.71 |

FOREIGN PATENT DOCUMENTS 0160272 11/1985 European Pat. Off. .

Primary Examiner—W. Gary Jones
Attorney, Agent, or Firm—Townsend and Townsend

[57] ABSTRACT

The invention relates to an apparatus for hemodialysis comprising a mixing means which prepares dialysis solution for a dialyzer by mixing concentrate with prepared water. The apparatus comprises a protective system which is independent of the mixing system and which is based on monitoring the conductivity of the dialysis solution. For protection against confusion of the concentrate containers to be connected, in the concentrate intake conduits conductivity measuring cells are additionally provided and the output signals thereof are compared with the desired values of the conductivity of the concentrates of the concentrate containers to be connected. In advantageous manner said conductivity cells are integrated into the concentrate intake conduits in such a way that they serve simultaneously as level sensors for the concentrate in the containers.

9 Claims, 3 Drawing Sheets

APPARATUS FOR HEMODIALYSIS

The invention relates to an apparatus for hemodialysis comprising a mixing means which prepares dialysis solution for a dialyzer by mixing at least one dialysis concentrate supplied via an intake conduit from a container with prepared water, and a protective system which is independent of the mixing system, is based on the monitoring of the conductivity of the dialysis solution and prevents dialysis solution with a composition dangerous to the patient reaching the dialyzer, as known for example from EP-A 160,272.

Hemodialysis apparatuses generally comprise a mixing means which prepares the dialysis solution for the dialyzer by mixing at least one dialysis concentrate with prepared water. The mixing means comprises intake plugs for the intake conduits of the concentrate containers.

Since such mixing means can fail the valid safety standards require a protective system which is independent of the mixing system and which prevents dialysis solution having a composition dangerous to the patient from reaching the dialyzer. Monitoring the conductivity of the dialysis solution is considered to be an adequate protective system (VDE 750/part 206).

Thus, it is known for example from EP-A 160,272 mentioned at the beginning to combine a volumetric mixing system with an independent protective system on the basis of monitoring the conductivity of the dialysis solution. This system offers adequate protection from dialysis with incorrect dialysis solution composition, even for the case of any initial error.

For medical reasons, in recent years hemodialysis with bicarbonate-containing dialysis solution has become widespread. In this case, for reasons of stability the dialysis solution must be prepared by mixing water with two concentrates.

Apart from the cases where two different concentrates are to be mixed with water with different mixture ratios, mixing means also exist in which only specific concentrate with predetermined mixing ratio is admixed.

As a rule, the concentrates are made ready in containers (cans). Now, since several different concentrates are present in a dialysis ward by mistaking concentrate cans an addition source of danger can occur. It has been shown that there are possibilities of confusion which lead to a composition of the dialysis solution which is dangerous to the patient and which cannot be detected by the conductivity protective system.

To avoid such risks it is known for connection of the concentrate containers to the intake plugs to provide "coded plugs" which ensure an unmistakable connection of the desired concentrate container to the associated intake plug. However, the system of coded plugs or connectors requires that the mixing means or the apparatus and the concentrate containers come from the same manufacturer because so far no standardization has been made in this respect. The safety by coded connectors is thus no longer ensured when concentrate containers of a different design are used.

It is further known to provide a protective system on a pH electrode basis.

Such a protective system has however only a restricted value because its function cannot be tested under the usual conditions of hemodialysis operation before starting the hemodialysis treatment as is possible with the other protective systems. In addition, the life of pH electrodes under the conditions of hemodialysis is as a rule less than one year.

The invention is based on the problem, proceeding from the apparatuses referred to at the beginning for hemodialysis comprising a mixing means which prepares dialysis solution for a dialyzer by mixing at least one dialysis concentrate supplied via an intake conduit from a container with prepared water, and a protective system which is independent of the mixing system, is based on the monitoring of the conductivity of the dialysis solution and prevents dialysis solution with a composition dangerous to the patient reaching the dialyzer, of further developing said apparatuses in such a manner that an effective protection can be obtained against incorrect composition of the dialysis solution due to the use of an incorrect dialysis concentrate.

This problem is solved according to the invention in that in the intake conduit an additional conductivity cell is disposed of which the output signal is applied to a monitoring stage of the protective system and at said stage the desired conductivity with correct connection of the dialysis concentrate container is preset and said stage emits an alarm or control signal when the measured conductivity due to an incorrect connection of the dialysis concentrate container deviates from the preset value.

Since each concentrate has a specific conductivity, i.e. the conductivity "identifies" the concentrate, it is ensured that connection of the wrong concentrate container is immediately detected.

The same applies when two concentrate containers with different concentrates have been interchanged.

The invention therefore provides an effective protective system against dialysis with incorrect composition of the dialysis solution due to incorrectly connected concentrate containers.

The invention will be explained in detail with reference to examples of embodiment illustrated in the drawings, wherein.

Figure 1:
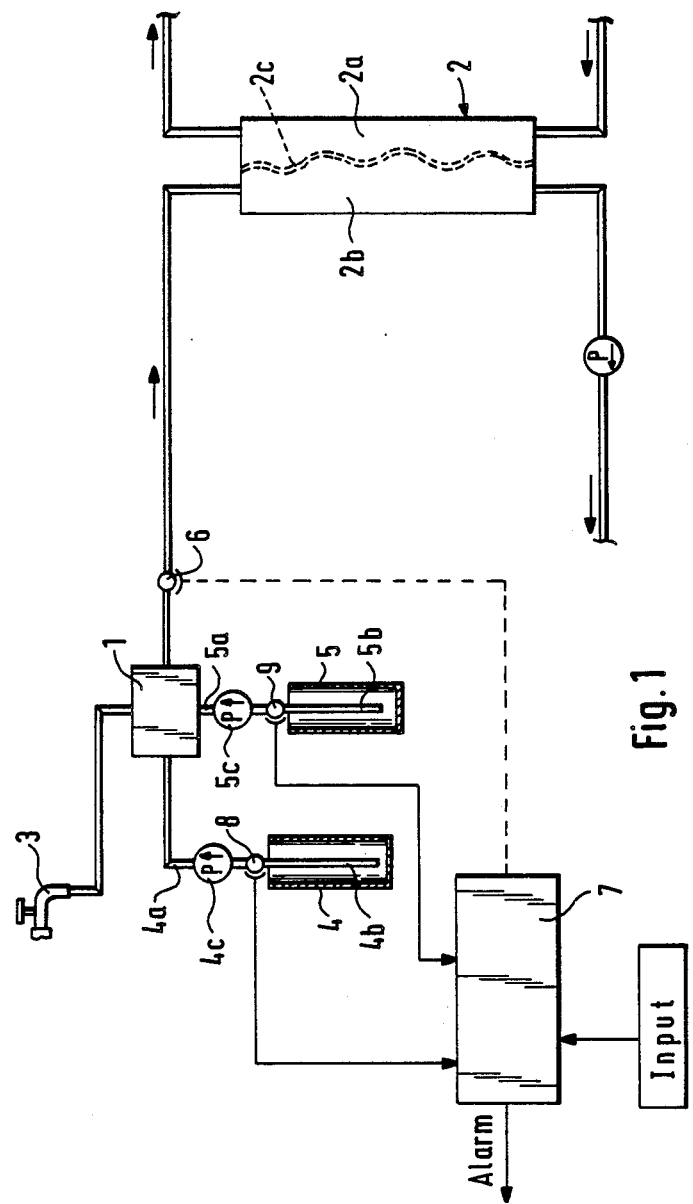
FIG. 1 shows a schematic representation of a hemodialysis apparatus in which the invention is employed.

In FIG. 1 an embodiment of an apparatus for hemodialysis according to the invention is shown. The apparatus comprises a mixing means 1 preparing dialysis solution for a dialyzer 2. Said dialyzer 2 consists in known manner of a blood section 2a and a dialysis solution section 2b which are separated by a membrane 2c.

The dialysis solution is prepared in known manner by mixing two dialysis concentrates with prepared water in the mixing means 1. The prepared water is taken from 3. The concentrates are accommodated in containers 4 and 5 into which intake tubes 4b, 5b dip and which are connected via intake flexible tubes 4a and 5a to the associated concentrate intake connectors at the mixing means 1.

The concentrates are delivered to the mixing means from the containers 4 and 5 via respective concentrate pumps 4c and 5c. The concentrate pumps 4c, 5c and the fresh water supply means are controlled by a control means which is not illustrated and which is known in the art.

For example, in one concentrate container the so-called "acid concentrate", an approximately 4-molar acid concentrate solution, is to be disposed and in the other container a bicarbonate concentrate (1-molar solution). To obtain the correct composition of the dialysis solution the first concentrate must be admixed in the ration 1:35 and the bicarbonate concentrate in the ratio 1:26 to the finished solution.

Since various concentrates are present in a dialysis ward an additional risk can occur in this respect by mistaking and confusion of concentrates.

6 denotes a conductivity measuring apparatus of a protective system which is independent of the mixing system and the output signal of which is applied to a monitoring circuit 7. In known manner the protective system prevents dialysis solution having a composition dangerous to the patient from reaching the dialyzer 2.

It has however been found that there are possibilities of getting concentrate containers mixed up which lead to a composition of the dialysis solution which is dangerous to the patient but which cannot be detected by the conductivity protective system with the cell 6.

To effectively exclude this additional risk in the intake section 4a, 4b; 5a, 5b a conductivity cell 8, 9 is disposed in each case and the output signal thereof is applied to the monitoring stage 7. The conductivities of the 1-molar bicarbonate solution and of the approximately 4-molar acid concentrate solution differ from each other to such an extent that even after taking account of all the tolerances to be incorporated there is a marked conductivity difference. Thus, for example, a temperature compensation can also be dispensed with because the deviations caused thereby are only of the order of magnitude of about 20-30%.

If instead of the absolute conductivity of the individual concentrate the ratio thereof is evaluated then the influence of different temperatures drops to a few %, assuming that both concentrates have the same temperature, as is generally the case.

Thus, by comparing the output signals emitted by the conductivity cells with the preset desired conductivity values concentrate confusions can be detected with certainty, in particular those which would lead to a dialysis solution having a conductivity in the expected range, i.e. which would not cause the higher-ranking protective system with the measuring cell 6 to respond because the measured conductivity of the dialysis solution lies in the desired range.

The signal deviations occurring in the monitoring stage can initiate a switching or control operation in the mixing means and/or an alarm signal.

The aim of a simple and reliable protective arrangement against concentrate mistakes is therefore achieved.

The invention is not restricted to the concentrate example given. It can also be used for all concentrates which exhibit a conductivity appreciably different from each other.

It is also possible to monitor additionally with the principle according to the invention mixing means of the type having only one concentrate intake connector or plug. The respective measured conductivity value of the connected concentrate is then compared with the desired value, set in the monitoring stage, of the conductivity of the concentrate actually to be excluded.

Figure 2:
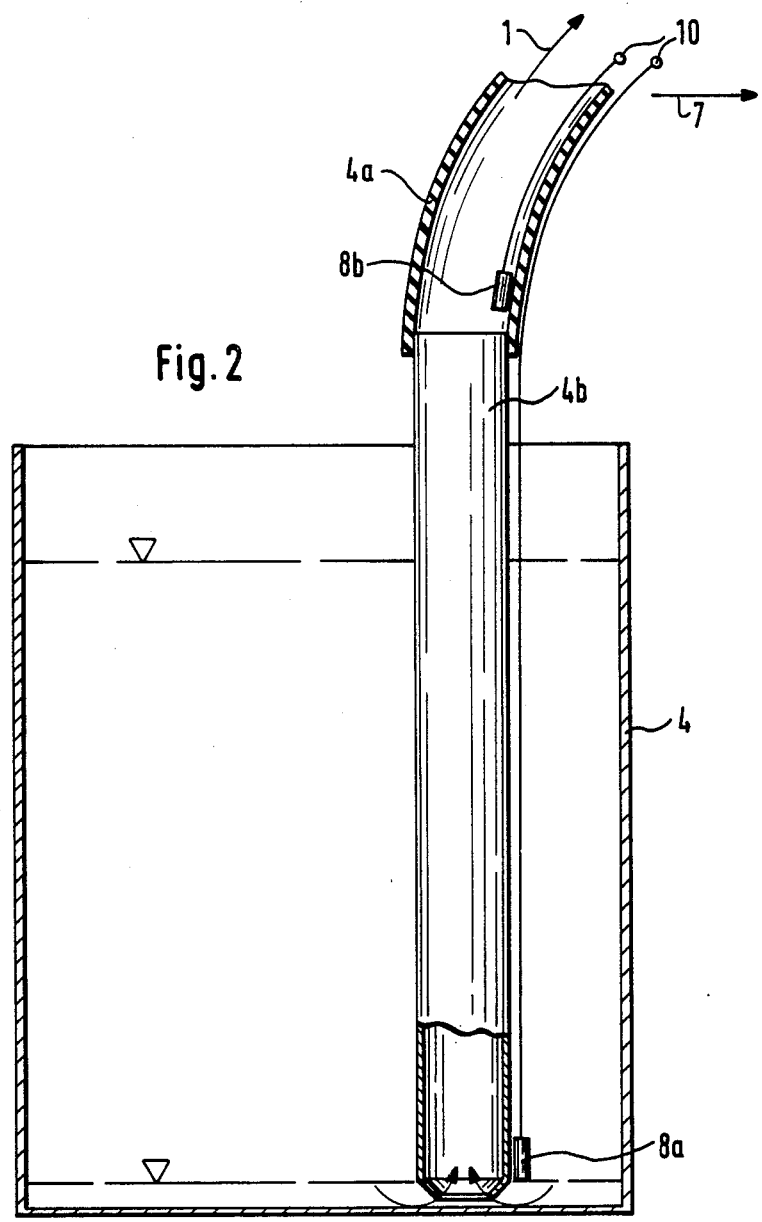
FIG. 2 is a schematic representation of one of the concentrate containers of FIG. 1.

According to a preferred embodiment of the invention, which is shown in FIG. 2, the electrodes of the conductivity cells are integrated in the concentrate intake conduits in such a manner that they can serve simultaneously as filling level sensors for the concentrate containers.

FIG. 2 shows the concentrate container 4 of FIG. 1 in an enlarged schematic illustration. The concentrate container is connected by means of the feed flexible tube 4a to the mixing means 1. The intake tube 4b dips into the concentrate and is made of a plastic material and in the lower region, indicated by the arrows, comprises the intake opening. Above said intake openings at the outside of the plastic tube the first electrode 8a of the conductivity cell is mounted. The second electrode 8b is disposed in the feed flexible tube 4a which does not dip into the concentrate solution.

When in operation concentrate is drawn into the interior of the intake tube 4b a measuring signal for the conductivity occurs at the terminals 10 as soon as the concentrate liquid column reaches the second electrode 8b. When the filling level in the container drops below the level of the first electrode 8a said signal is interrupted and an alarm signal can be generated before the concentrate container is empty.

Such level monitorings in concentrate containers are known per se; in the known case contactless proximity switches are additionally provided for detecting the level. In the case of the invention however the simultaneous use of the electrodes 8a, 8b for conductivity measurement and for level supervision is significant.

Figure 3:
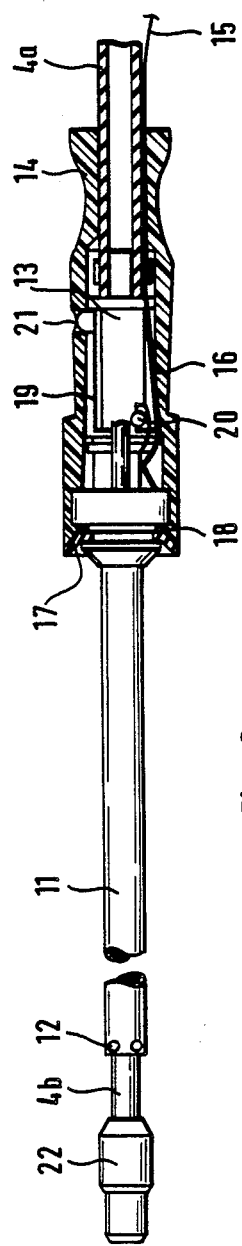
FIG. 3 shows a partially sectioned illustration of a complete outlet conduit.

FIG. 3 shows a partially sectioned illustration of a complete intake tube which in contrast to the intake conduit according to FIG. 2 does not have a conductivity cell as such but in which the conductivity is registered via an electrically conductive metal tube 11 and the radial outlet openings 12 thereof in the monitoring circuit 7 and displayed these simultaneously serving as filling level meter. In accordance with this embodiment the feed flexible tube 4a merges at its front end into an intermediate clamping piece 13 which is again connected to the outlet tube 4b. This transition point is surrounded by a grip member 14 which consists of plastic. Over almost the entire region of the intake tube 4b the latter is enclosed by an electrically conductive metal tube 11 which at its rear end is likewise connected in electrically insulated manner to the intermediate clamping member 13. The electrically conductive metal tube 11 serves as electrode and via a contact spring 16 disposed in the grip member 14 is in connection with a contact line 15 disposed in the flexible feed tube 4a. The grip member 14 is sealed with respect to the metal tube 11 by means of a sealing disk 17 so as to be sealed as regards the concentrate agent to prevent any concentrate solution reaching the interior of the grip member 14. Said sealing disk or sealing washer 17 is fixed by a spacer ring 18.

Furthermore, in the grip member 14 a detent element 19 is provided which is pivotal via a pin 20 and can engage into a grip opening 21. This makes it possible on actuating the detent element 18 to remove the latter as desired together with the electrically conductive metal tube from the holder of the grip member 14 and to insert a different intake tube and/or metal tube.

A portion of the intake tube 4b on which a coding jack 22 is disposed which seals the front end of the intake tube 4b extends at the front end of the metal tube 11 in the region of the intake openings 12, which may be made O-ring shaped and ensure a flow connection from the outer space to the inner space of the intake tube 4b. Said connector serves to engage into a corresponding counter member disposed in the concentrate container to exclude any confusion of the concentrate containers with the corresponding feed flexible tube. For this purpose each coding connector has a different form or a different cross-section, for example circular or rectangular.

A corresponding conductivity is registered in the monitoring circuit 7. The contact line 15 and the metal tube 11 carry current. Now, if the concentrate level drops beneath the intake openings 12 there is no longer any conductivity between the concentrate in the solution container and the metal tube 11 so that the absence of the conductivity is reported via the contact line 15 to the monitoring circuit 7 which generates a corresponding alarm signal before the concentrate container is empty. The electrical conductivity thus also serves to monitor the filling level because the intake openings 12 at the front end of the metal tube 11 perform the function of a conductivity cell.

I claim:

1. In an apparatus for hemodialysis which comprises a mixing system for supplying dialysis solution to a dialyzer (2) and a protective system (6, 7) independent of the mixing system for preventing the dialyzer from receiving dialysis solution which is dangerous to a patient, wherein the mixing system includes at least one source container for dialysis concentrate (4,5), at least one intake conduit (4a, 4b; 5a, 5b), a source of water (3), and a mixing means (1), and wherein said protective system includes a first conductivity cell (6) for monitoring conductivity of dialysis solution and at least a first monitoring stage, the improvement comprising:
   at least one second conductivity cell (8, 9) in said intake conduit; and
   a second protective system (8, 9, 7) comprising a means for monitoring a conductivity of dialysis concentrate through said second conductivity cell to apply an output signal from said second conductivity cell to a monitoring stage of said second protective system where a correct connection of the source container of dialysis concentrate exists and conductivity measured by said second conductivity cell is within a preset range and to emit an alarm or control signal from said monitoring stage of said second protective system where measured conductivity deviates from said preset range in order to detect incorrect connection of said dialysis concentrate container.

2. Apparatus according to claim 1 wherein at least two dialysis concentrate containers exist, and wherein the monitoring stage (7) of the second protective system further comprises means for responding to the ratio of the output signals of at least two second conductivity cells.

3. Apparatus according to claim 1 or 2, wherein the second conductivity cells (8,9) are integrated into the intake conduit (4a,b; 5a,b) in such a manner that they serve simultaneously as filling level sensors for the dialysis concentrate container.

4. Apparatus according to claim 3 wherein the intake conduit comprises a feed flexible tube (4a, 5a) not dipping into the dialysis concentrate and an intake tube (4b, 5b) dipping into the dialysis concentrate, wherein the intake tube (4b, 5b) comprises a plastic material and located outside and above an intake opening carries a first electrode (8a) of the second conductivity cell, wherein a second electrode (8b) of said second conductivity cell is located inside the feed flexible tube (4a).

5. Apparatus according to claim 1 wherein an intake conduit (4a, 4b) comprises a feed flexible tube (4a) not dipping into the dialysis concentrate and an intake tube (4b) dipping into the dialysis concentrate, wherein the intake tube (4b) further comprises an electrically conductive tube (11) which serves as electrode and is connected via a line (15) to the monitoring stage of the second protective system (7).

6. Apparatus according to claim 5, wherein the intake tube (4b) is additionally provided at its front end with a coding jack (22) which engages into a corresponding counter member in the dialysis concentrate container.

7. Apparatus according to claim 5 or 6, wherein the intake tube (4b) is connected detachably via a contact spring (16) to the line (15) and via detent elements (20, 21) to a grip member (13).

8. Apparatus according to claim 6 or 7, wherein the front end of the intake tube (4b) is sealed by the coding jack (22) and in a region of said front end, radial openings (12) are provided which ensure a flow connection from inside the intake tube to outside the intake tube (4b).

9. In a method for hemodialysis using a hemodialysis apparatus which comprises a mixing system for supplying dialysis solution to a dialyzer and a protective system independent of the mixing system for preventing the dialyzer from receiving dialysis solution which is dangerous to a patient, wherein said mixing system includes at least one source container for dialysis concentrate, at least one intake conduit, a source of water, and a mixing means, and wherein said protective system includes a first conductivity cell for sensing conductivity of dialysis solution and a monitoring stage for monitoring conductivity of dialysis solution through said first conductivity cell, said method including the steps of mixing dialysis concentrate from said source container with water from said source of water to produce the dialysis solution, monitoring the conductivity of the dialysis solution through said first conductivity cell and preventing dialysis solution having a composition dangerous to the patient from reaching the dialyzer, the improvement comprising:
   providing at least one second conductivity cell in said intake conduit;
   monitoring conductivity of the dialysis concentrate through said second conductivity cell;
   applying an output signal from said second conductivity cell to a monitoring stage of a second protective system where correct connection of the dialysis concentrate container exists and conductivity measured by said second conductivity cell is within a preset range; and
   emitting an alarm or control signal from said second protective system where measured conductivity deviates from said preset range.

* * * * *